United States Patent
Dacosta et al.

(10) Patent No.: US 11,426,341 B2
(45) Date of Patent: *Aug. 30, 2022

(54) ALKYL POLYRHAMNOSIDES, PROCESS FOR THE PREPARATION THEREOF, AND COSMETIC AND/OR PHARMACEUTICAL COMPOSITION COMPRISING SAME

(71) Applicant: SOCIETE D'EXPLOITATION DE PRODUITS POUR LES INDUSTRIES CHIMIQUES SEPPIC, Paris (FR)

(72) Inventors: Georges Manuel Dacosta, Saix (FR); Stéphane Dessilla, Castres (FR); Jerome Guilbot, Castres (FR); Virginie Pommery, Garrigues (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 173 days.

This patent is subject to a terminal disclaimer.

(21) Appl. No.: 16/772,415

(22) PCT Filed: Dec. 4, 2018

(86) PCT No.: PCT/FR2018/053102
§ 371 (c)(1),
(2) Date: Jun. 12, 2020

(87) PCT Pub. No.: WO2019/115911
PCT Pub. Date: Jun. 20, 2019

(65) Prior Publication Data
US 2021/0069085 A1   Mar. 11, 2021

(30) Foreign Application Priority Data

Dec. 12, 2017 (FR) ...................... 1762000

(51) Int. Cl.
*A61K 8/60* (2006.01)
*A61K 8/19* (2006.01)
*A61K 8/34* (2006.01)
*A61K 8/365* (2006.01)
*A61K 8/37* (2006.01)
*A61K 8/41* (2006.01)
*A61K 8/49* (2006.01)
*A61K 8/891* (2006.01)
*A61Q 1/14* (2006.01)
*A61Q 5/02* (2006.01)
*A61Q 19/10* (2006.01)

(52) U.S. Cl.
CPC ............ *A61K 8/604* (2013.01); *A61K 8/19* (2013.01); *A61K 8/347* (2013.01); *A61K 8/365* (2013.01); *A61K 8/37* (2013.01); *A61K 8/41* (2013.01); *A61K 8/498* (2013.01); *A61K 8/4946* (2013.01); *A61K 8/602* (2013.01); *A61K 8/891* (2013.01); *A61Q 1/14* (2013.01); *A61Q 5/02* (2013.01); *A61Q 19/10* (2013.01)

(58) Field of Classification Search
None
See application file for complete search history.

(56) References Cited

FOREIGN PATENT DOCUMENTS

| | | |
|---|---|---|
| EP | 0 971 683 A1 | 1/2000 |
| EP | 0 977 626 B1 | 10/2002 |
| FR | 2899099 | 10/2007 |
| WO | 94/26694 A1 | 11/1994 |
| WO | 96/00719 A1 | 1/1996 |
| WO | 98/09611 A1 | 3/1998 |
| WO | 98/44902 A1 | 10/1998 |
| WO | 2005/040230 A2 | 5/2005 |

OTHER PUBLICATIONS

International Search Report, PCT/FR2018/053102, dated Apr. 1, 2019.
French Search Report, FR 1762000 dated Oct. 1, 2018.

*Primary Examiner* — Nicole P Babson
(74) *Attorney, Agent, or Firm* — Nixon & Vanderhye

(57) ABSTRACT

Composition based on fatty alcohols and on alkyl polyrhamnosides; process for the preparation thereof; cosmetic or pharmaceutical composition comprising same; and use thereof as an emulsifier.

17 Claims, No Drawings

ALKYL POLYRHAMNOSIDES, PROCESS FOR THE PREPARATION THEREOF, AND COSMETIC AND/OR PHARMACEUTICAL COMPOSITION COMPRISING SAME

BACKGROUND OF THE INVENTION

Field of the Invention

The present invention relates to a novel composition based on sugar derivatives, to the process for preparing same and to the use thereof as emulsifier.

Description of the Related Art

The invention mainly finds application in cosmetics and pharmaceuticals. Emulsifying surfactants derived from reducing sugars, and more particularly from glucose or xylose, have been widely described in the literature. Many of them are notably marketed under the brand names Montanov™, Simulgreen™ 18/2, Easynov™ and Fluidanov™ 20X. They are compositions comprising linear or branched fatty alcohols, which may include at least one hydroxyl function, and including between 14 and 22 carbon atoms and alkyl polyglucosides or alkyl polyxylosides, the alkyl chain of which itself also includes from 14 to 22 carbon atoms. Such compositions generally do not comprise more than 40% by mass of alkyl polyglycosides since the production of compositions with a higher concentration of alkyl polyglycosides requires a subsequent step either of distillation of fatty alcohols, or a step of extraction with a fluid in supercritical form, which are both energy-intensive.

SUMMARY OF THE INVENTION

In the context of their research with regard to improving oil-in-water emulsions, the inventors focused on developing a novel technical solution based on the use of a natural sugar, rhamnose, the natural source of which is wood hemicellulose, notably that from birch or from beech:

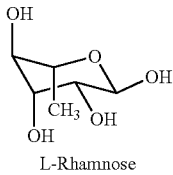

L-Rhamnose

Thus, according to a first aspect, one subject of the invention is a composition ($C_1$) comprising, per 100% of its mass:

(a)—an amount of greater than 0% by mass and less than or equal to 60% by mass of an alcohol of formula (I): R—OH, in which R represents a linear or branched, saturated or unsaturated hydrocarbon-based radical, which may include at least one hydroxyl function, and including from 14 to 22 carbon atoms or a mixture of alcohols of formula (I);

(b)—an amount of greater than or equal to 40% and less than 100% by mass of a composition ($C_R$) represented by formula (II): R—O-(Rham)$_x$-H, in which the Rham residue represents the rhamnose residue, R is as defined previously in formula (I) and x, which indicates the average degree of polymerization of said Rham residue, represents a decimal number greater than 1.0 and less than or equal to 5; or a mixture of compositions ($C_R$), and (c)—optionally an amount of greater than 0% by mass and less than or equal to 5% by mass of rhamnose.

The term "saturated or unsaturated linear hydrocarbon-based aliphatic radical, which may include at least one hydroxyl function, and including from 14 to 22 carbon atoms" more particularly denotes for R, in formula (I) as defined previously:

either a radical derived from saturated or unsaturated linear primary alcohols, such as the myristyl (or tetradecyl), pentadecyl, cetyl (or hexadecyl), heptadecyl, stearyl (or octadecyl), palmitoleyl (or 9-hexadecenyl), oleyl (or 9-octadecenyl), linoleyl (9,12-octadecadienyl), linolenyl (or 6,9,12-octadecatrienyl) nonadecyl, arachidyl (or eicosyl), behenyl (or docosyl), erucyl (13-docosenyl) or 12-hydroxystearyl radical;

or a radical derived from saturated branched alcohols, such as the 2-hexyloctyl, 2-hexyldecyl, 2-hexyldodecyl, 2-octyldecyl, 2-octyldodecyl, 2-hexyldodecyl, 2-decyltetradecyl or 2-octyldecyl isostearyl (or 16-methylheptadecyl) or isomyristyl (or 13-methyl tridecyl) radicals.

The term "formula (II): R—O-(Rham)$_x$-H" means that said composition ($C_R$) consists essentially of a mixture of compounds represented by formulae (II$_1$), (II$_2$), (II$_3$), (II$_4$) and (II$_5$):

R—O-(Rham)$_1$-H  (II$_1$),

R—O-(Rham)$_2$-H  (II$_2$),

R—O-(Rham)$_3$-H  (II$_3$),

R—O-(Rham)$_4$-H  (II$_4$),

R—O-(Rham)$_5$-H  (II$_5$), in the respective molar proportions $a_1$, $a_2$, $a_3$, $a_4$ and $a_5$, such that the sum $a_1+a_2+a_3+a_4+a_5$ is equal to 1 and such that the sum $a_1+2a_2+3a_3+4a_4+5a_5$ is equal to x.

In the preceding definition, the term "essentially" indicates that the presence of one or more compounds of formula (II$_w$) with w greater than 5 is not excluded in composition ($C_R$), but that if it is present, then it is present in minimal proportions which do not entail any substantial modification of the properties of said composition ($C_R$).

In formula (II) as defined above, the group R—O— is linked to (Rham)$_x$ via the anomeric carbon of the saccharide residue, so as to form an acetal function.

The subject of the invention is mainly composition (C1) as defined previously, for which, in formulae (I) and (II), R represents a linear or branched, saturated or unsaturated hydrocarbon-based radical including from 16 to 20 carbon atoms; and more particularly from 16 to 18 carbon atoms, such as the composition comprising, per 100% of its mass:

(a)—an amount of greater than 0% by mass and less than or equal to 60% by mass of a mixture ($M_1$) comprising, per 100% of its mass:

from 30% by mass to 70% by mass of an alcohol of formula ($I_A$): $R_A$—OH, in which $R_A$ represents a hexadecyl radical, and from 70% by mass to 30% by mass of an alcohol of formula ($I_B$): $R_B$—OH, in which $R_B$ represents an octadecyl radical;

(b)—an amount of greater than or equal to 40% and less than 100% by mass of a mixture ($M_{CR1}$) comprising, per 100% of its mass:

from 30% to 70% by mass of a composition ($C_{RA}$) represented by formula ($II_A$): $R_A$—O-(Rham)$_y$-H, in which the Rham residue represents the rhamnose residue, $R_A$ is as defined previously in formula ($I_A$) and y represents a decimal number greater than 1.0 and less than or equal to 5; and from 70% to 30% by mass of a composition ($C_{RB}$) represented by formula ($II_B$): $R_B$—O-(Rham)$_z$-H, in which the Rham residue represents the rhamnose residue, $R_B$ is as defined previously in formula ($I_B$) and Z represents a decimal number greater than 1.0 and less than or equal to 5; and (c)—optionally an amount of greater than 0% by mass and less than or equal to 5% by mass of rhamnose.

The subject of the invention is also more particularly composition (C1) as defined previously, for which, in formulae (I) and (II), R represents a linear or branched, saturated or unsaturated hydrocarbon-based radical including from 20 to 22 carbon atoms, such as the composition comprising, per 100% of its mass:

(a)—an amount of greater than 0% by mass and less than or equal to 60% by mass of a mixture ($M_2$) comprising, per 100% of its mass:

from 30% by mass to 70% by mass of an alcohol of formula ($I_C$): $R_C$—OH, in which $R_C$ represents an eicosyl radical, and from 70% by mass to 30% by mass of an alcohol of formula ($I_D$): $R_D$—OH, in which $R_D$ represents a docosyl radical;

(b)—an amount of greater than 40% by mass and less than 100% by mass of a mixture ($M_{CR2}$) comprising, per 100% of its mass:

from 30% to 70% by mass of a composition ($C_{RC}$) represented by formula ($II_C$): $R_C$—O-(Rham)$_t$-H, in which the Rham residue represents the rhamnose residue, $R_C$ is as defined previously in formula ($I_C$) and t represents a decimal number greater than 1.0 and less than or equal to 5; and from 70% to 30% by mass of a composition ($C_{RD}$) represented by formula ($II_D$): $R_D$—O-(Rham)$_u$-H, in which the Rham residue represents the rhamnose residue, $R_D$ is as defined previously in formula ($I_D$) and u represents a decimal number greater than 1.0 and less than or equal to 5; and (c)—optionally an amount of greater than 0% by mass and less than or equal to 5% by mass of rhamnose.

According to another particular aspect, composition ($C_1$) as defined previously comprises, per 100% of its mass:

(a)—an amount of greater than 0% by mass and less than or equal to 40% by mass of said alcohol of formula (I) or of said mixture of alcohols of formula (I);

(b)—an amount of greater than or equal to 60% by mass and less than 100% by mass of said composition ($C_R$) or of said mixture of compositions ($C_R$);

(c)—optionally an amount of greater than 0% by mass and less than or equal to 5% by mass of rhamnose; and more particularly:

(a)—an amount of greater than 0% by mass and less than or equal to 20% by mass of said alcohol of formula (I) or of said mixture of alcohols of formula (I);

(b)—an amount of greater than or equal to 80% by mass and less than 100% by mass of said composition ($C_R$) or of said mixture of compositions ($C_R$);

(c)—optionally an amount of greater than 0% by mass and less than or equal to 3% by mass of rhamnose.

According to another particular aspect, composition ($C_1$) as defined previously is characterized in that, in formulae (II), ($II_A$), ($II_B$), ($II_C$) and ($II_D$), the respective numbers x, y, z, t and u each represent a decimal number greater than zero and less than or equal to 2. One subject of the invention is also a process for preparing composition ($C_1$) as defined in any one of claims 1 to 9, characterized in that it comprises the following successive steps:

a step a) of heating, with moderate stirring, the alcohol of formula (I) as defined previously or of a mixture of said alcohols of formula (I), until it is brought to a higher temperature ($T_1$) of at least 5° C. above its melting point;

a step b) of dispersing, with stirring, rhamnose monohydrate in the previously molten medium in the desired stoichiometric ratio;

a step c) of acetalization by adding, with stirring, to the liquid medium obtained from step b), a catalytic amount of strong acid, while maintaining all the reaction mixture under partial vacuum and distilling off the water formed;

a step d) of filtering the reaction mixture obtained in step c), and, if necessary or if desired, a step e) of neutralizing the solution obtained on conclusion of step d), to obtain said composition ($C_1$).

For the purposes of the present invention, the term "moderate stirring" means mechanical stirring consisting of a stirrer equipped with an "anchor" type or "impeller" type paddle, set at a speed of greater than or equal to 50 rpm and less than or equal to 150 rpm and more particularly greater than or equal to 80 rpm and less than or equal to 150 rpm and even more particularly greater than or equal to 80 rpm and less than or equal to 120 rpm.

For the implementation of step c) as defined above, the strong acid is notably chosen from sulfuric acid, hydrochloric acid, phosphoric acid, nitric acid, hypophosphorous acid, methanesulfonic acid, para-toluenesulfonic acid, trifluoromethanesulfonic acid and acidic ion-exchange resins.

According to a preferred aspect of the process as defined above, the catalytic system used in step c) is a mixture of 98% sulfuric acid and hypophosphorous acid or a mixture of 98% sulfuric acid supported on silica and hypophosphorous acid.

Usually, in step c), the acetalization reaction is performed at a temperature ($T_2$) from 70° C. to 105° C., under a vacuum of from 300 to $20 \times 10^2$ Pa (300 to 20 mbar). The filtration step d) of the process as defined above is generally performed under hot conditions to keep the mixture to be filtered in sufficiently liquid form.

Composition ($C_1$) as defined previously may be used as emulsifier of oil-in-water type for preparing any type of cosmetic or pharmaceutical composition intended to be applied to the skin or mucous membranes in oil-in-water emulsion form.

This is why one subject of the invention is also an emulsion of topical cosmetic or dermocosmetic oil-in-water type (C), characterized in that it comprises as emulsifier an effective amount of composition ($C_1$) as defined previously; and also an emulsion of topical pharmaceutical or dermopharmaceutical oil-in-water type (C'), characterized in that it comprises as emulsifier an effective amount of composition ($C_1$) as defined previously; and finally the use of composition ($C_1$) as defined previously as emulsifier for preparing emulsions of oil-in-water type.

In the definitions of the abovementioned emulsions of oil-in-water type (C) and (C'), the term "effective amount" denotes a mass proportion generally greater than or equal to 2.0% by mass and less than or equal to 5.0%, relative to their total mass and more particularly from 2.5% by mass to 4.0% by mass relative to their total mass.

The adjective "topical" qualifying the abovementioned emulsions of oil-in-water type (C) and (C') means that these emulsions are used by application to the skin, the scalp or mucous membranes.

Said abovementioned emulsions of oil-in-water type (C) and (C') may be used as cream, milk, bubble bath, shampoo, hair conditioner or lotion for caring for or protecting the face, the hands and the body, more particularly for their short-term moisturizing effect on the epidermis after prolonged exposure to low temperatures, or to solar radiation; or alternatively for preventing or slowing down the appearance of the external signs of aging of human skin, for instance the appearance of wrinkles, fine lines, impairment of the microrelief, lack of elasticity and/or tonicity, lack of density and/or firmness of human skin; or alternatively after shaving the face or for washing and/or treating the scalp.

In general, said emulsions of oil-in-water type (C) and (C') also include excipients and/or active principles usually used in the field of topical formulations, for instance foaming and/or detergent surfactants, thickening and/or gelling surfactants, thickeners and/or gelling agents, stabilizers, film-forming compounds, solvents and cosolvents, hydrotropic agents, plasticizers, fatty substances, oils and waxes, emulsifiers and coemulsifiers, opacifiers, nacreous agents, overfatting agents, sequestrants, chelating agents, antioxidants, fragrances, essential oils, preserving agents, conditioning agents, bleaching agents intended for bleaching bodily hair and the skin, active principles intended to provide a treating and/or protective action to the skin or the hair, sunscreens, mineral fillers or pigments, particles that give a visual effect or that are intended for encapsulating active agents, exfoliant particles, texture agents, optical brighteners and insect repellents.

As examples of foaming and/or detergent surfactants optionally present in said emulsions of oil-in-water type (C) and (C') as defined previously, mention may be made of the topically acceptable anionic, cationic, amphoteric or nonionic foaming and/or detergent surfactants commonly used in this field of activity.

Among the foaming and/or detergent anionic surfactants optionally present in said emulsions of oil-in-water type (C) and (C') as defined previously, mention may be made of alkali metal salts, alkaline-earth metal salts, ammonium salts, amine salts and amino alcohol salts, of alkyl ether sulfates, of alkyl sulfates, of alkylamido ether sulfates, of alkylaryl polyether sulfates, of monoglyceride sulfates, of α-olefin sulfonates, of paraffin sulfonates, of alkyl phosphates, of alkyl ether phosphates, of alkylsulfonates, of alkylamide sulfonates, of alkylarylsulfonates, of alkylcarboxylates, of alkylsulfosuccinates, of alkyl ether sulfosuccinates, of alkylamide sulfosuccinates, of alkylsulfoacetates, of alkylsarcosinates, of acylisethionates, of N-acyltaurates, of acyllactylates, of N-acyl derivatives of amino acids, of N-acyl derivatives of peptides, of N-acyl derivatives of proteins, of fatty acids.

Among the foaming and/or detergent amphoteric surfactants optionally present in said emulsions of oil-in-water type (C) and (C') as defined previously, there are alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants optionally present in said emulsions of oil-in-water type (C) and (C') as defined previously, there are in particular quaternary ammonium derivatives.

Among the foaming and/or detergent nonionic surfactants optionally present in said emulsions of oil-in-water type (C) and (C') as defined previously, there are more particularly alkylpolyglycosides, castor oil derivatives, polysorbates, coconut kernel amides and N-alkylamines.

Among the foaming and/or detergent nonionic surfactants optionally present in said emulsions of oil-in-water type (C) and (C') as defined previously, there is more particularly composition $(C_3)$ or a mixture of compositions $(C_3)$, said composition $(C_3)$ being represented by formula (IV):

$$R_2\text{—}O\text{-}(G_2)_p\text{-}H \qquad (IV)$$

in which $R_2$ represents a linear or branched, saturated or unsaturated aliphatic radical including from 8 to 16 carbon atoms, $G_2$ represents a reducing sugar residue and p represents a decimal number greater than or equal to 1.05 and less than or equal to 5, said composition $(C_3)$ consisting essentially of a mixture of compounds represented by formulae $(IV_1)$, $(IV_2)$, $(IV_3)$, $(IV_4)$ and $(IV_5)$:

$$R_2\text{—}O\text{-}(G_2)_1\text{-}H \qquad (IV_1),$$

$$R_2\text{—}O\text{-}(G_2)_2\text{-}H \qquad (IV_2),$$

$$R_2\text{—}O\text{-}(G_2)_3\text{-}H \qquad (IV_3),$$

$$R_2\text{—}O\text{-}(G_2)_4\text{-}H \qquad (IV_4),$$

$$R_2\text{—}O\text{-}(G_2)_5\text{-}H \qquad (IV_5),$$

in the respective molar proportions $a_1$, $a_2$, $a_3$, $a_4$ and $a_5$, such that the sum $a_1+a_2+a_3+a_4+a_5$ is equal to 1 and such that the sum $a_1+2a_2+3a_3+4a_4+5a_5$ is equal to p.

As examples of thickening and/or gelling surfactants optionally present in said emulsions of oil-in-water type (C) and (C') as defined previously, mention may be made of optionally alkoxylated alkylpolyglycoside fatty esters, and most particularly ethoxylated methylpolyglucoside esters, such as the PEG 120 methyl glucose trioleate or the PEG 120 methyl glucose dioleate sold, respectively, under the names Glutamate™ LT and Glutamate™ DOE120; alkoxylated fatty esters, such as the PEG 150 pentaerythrityl tetrastearate sold under the name Crothix™ DS53, the PEG 55 propylene glycol oleate sold under the name Antil™ 141; fatty-chain polyalkylene glycol carbamates, such as the PPG14 laureth isophoryl dicarbamate sold under the name Elfacos™ T211, the PPG14 palmeth 60 hexyl dicarbamate sold under the name Elfacos™ GT2125.

As examples of emulsifying anionic surfactants optionally present in said emulsions of oil-in-water type (C) and (C') as defined previously, mention may be made of decyl phosphate, cetyl phosphate sold under the name Amphisol™, glyceryl stearate citrate; cetearyl sulfate; the arachidyl/behenyl phosphates and arachidyl/behenyl alcohols composition sold under the name Sensanov™ WR; soaps, for instance sodium stearate or triethanolammonium stearate, salified N-acylamino acid derivatives, for instance stearoyl glutamate.

As examples of emulsifying cationic surfactants optionally present in said emulsions of oil-in-water type (C) and (C') as defined previously, mention may be made of amine oxides, Quaternium™ 82 and the surfactants described in the international application published under the number WO 96/00719 and mainly those whose fatty chain comprises at least 16 carbon atoms.

As examples of opacifiers and/or nacreous agents optionally present in said emulsions of oil-in-water type (C) and (C') as defined previously, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate and fatty alcohols including from 12 to 22 carbon atoms.

As examples of texture agents optionally present in said emulsions of oil-in-water type (C) and (C') as defined previously, mention may be made of N-acylamino acid derivatives, for example lauroyl lysine sold under the name Aminohope™ LL, the octenyl starch succinate sold under the name Dryflo™, the myristyl polyglucoside sold under the name Montanov™ 14, cellulose fibers, cotton fibers, chitosan fibers, talc, sericite and mica.

As examples of solvents and cosolvents optionally present in said emulsions of oil-in-water type (C) and (C') as defined previously, mention may be made of water, ethylene glycol, propylene glycol, butylene glycol, hexylene glycol, diethylene glycol, water-soluble alcohols such as ethanol, isopropanol or butanol, and mixtures of water and of said solvents.

As examples of oils optionally present in said emulsions of oil-in-water type (C) and (C') as defined previously, mention may be made of mineral oils such as liquid paraffin, liquid petroleum jelly, isoparaffins or white mineral oils; oils of animal origin such as squalene or squalane; plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cotton oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty-leaf oil, sisymbrium oil, avocado oil, calendula oil, oils derived from flowers or vegetables; ethoxylated plant oils; synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, for instance glyceryl triheptanoate, alkylbenzoates, hydrogenated oils, poly(α-olefins), polyolefins such as poly(isobutane), synthetic isoalkanes, for instance isohexadecane, isododecane, perfluorinated oils; silicone oils, for instance dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. In the present application, the term "oils" refers to compounds and/or mixtures of compounds which are water-insoluble, and which have a liquid appearance at a temperature of 25° C.

As examples of waxes optionally present in said emulsions of oil-in-water type (C) and (C') as defined previously, mention may be made of beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; plant waxes; fatty alcohols and fatty acids that are solid at room temperature;

glycerides that are solid at room temperature. In the present application, the term "waxes" refers to compounds and/or mixtures of compounds which are water-insoluble, and which have a solid appearance at a temperature of greater than or equal to 45° C.

As examples of fatty substances optionally present in said emulsions of oil-in-water type (C) and (C') as defined previously, mention may be made of saturated or unsaturated, linear or branched fatty alcohols including from 8 to 36 carbon atoms, or saturated or unsaturated, linear or branched fatty acids including from 8 to 36 carbon atoms.

As examples of thickeners and/or gelling agents optionally present in said emulsions of oil-in-water type (C) and (C') as defined previously, there are linear or branched or crosslinked polymers of polyelectrolyte type, such as the partially or totally salified acrylic acid homopolymer, the partially or totally salified methacrylic acid homopolymer, the partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris(hydroxymethyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates the carbon chain of which comprises between 4 and 30 carbon atoms and more particularly between 10 and 30 carbon atoms, copolymers of AMPS and of alkyl acrylates the carbon chain of which comprises between 4 and 30 carbon atoms and more particularly between 10 and 30 carbon atoms, linear, branched or crosslinked terpolymers of at least one monomer having a free, partially salified or totally salified strong acid function, with at least one neutral monomer, and at least one monomer of formula (V):

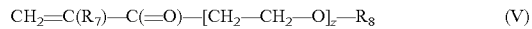

$$CH_2=C(R_7)-C(=O)-[CH_2-CH_2-O]_z-R_8 \qquad (V)$$

in which $R_7$ represents a hydrogen atom or a methyl radical, $R_8$ represents a linear or branched alkyl radical including from 8 to 30 carbon atoms and z represents a number greater than or equal to 1 and less than or equal to 50.

The linear or branched or crosslinked polymers of polyelectrolyte type optionally present in said emulsions of oil-in-water type (C) and (C') as defined previously may be in the form of a solution, an aqueous suspension, a water-in-oil emulsion, an oil-in-water emulsion or a powder. The linear or branched or crosslinked polymers of polyelectrolyte type optionally present in said emulsions of oil-in-water type (C) and (C') as defined previously may be chosen from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™ EMT 10, Sepiplus™ 400, Sepiplus™ 265, Sepiplus™ S, Sepimax™ Zen, Aristoflex™ AVC, Aristoflex™ AVS, Novemer™ EC-1, Novemer™ EC 2, Aristoflex™ HMB, Cosmedia™ SP, Flocare™ ET 25, Flocare™ ET 75, Flocare™ ET 26, Flocare™ ET 30, Flocare™ ET 58, Flocare™ PSD 30, Viscolam™ AT 64 and Viscolam™ AT 100.

As examples of thickeners and/or gelling agents optionally present in said emulsions of oil-in-water type (C) and (C') as defined previously, there are polysaccharides consisting only of monosaccharides, such as glucans or glucose homopolymers, glucomannoglucans, xyloglycans, galactomannans of which the degree of substitution (DS) of the D-galactose units on the main D-mannose chain is between 0 and 1, and more particularly between 1 and 0.25, such as galactomannans originating from cassia gum (DS=1/5), locust bean gum (DS=1/4), tara gum (DS=1/3), guar gum (DS=1/2) or fenugreek gum (DS=1).

As examples of thickeners and/or gelling agents optionally present in said emulsions of oil-in-water type (C) and (C') as defined previously, mention may be made of polysaccharides consisting of monosaccharide derivatives, such as sulfated galactans and more particularly carrageenans and agar, uronans and more particularly algins, alginates and pectins, heteropolymers of monosaccharides and uronic acids, and more particularly xanthan gum, gellan gum, gum arabic exudates and karaya gum exudates, glucosaminoglycans.

As examples of thickeners and/or gelling agents optionally present in said emulsions of oil-in-water type (C) and (C') as defined previously, there is cellulose, cellulose derivatives such as methylcellulose, ethylcellulose, hydroxypropylcellulose, silicates, starch, hydrophilic starch derivatives and polyurethanes.

As examples of stabilizers optionally present in said emulsions of oil-in-water type (C) and (C') as defined previously, there are monocrystalline waxes, and more particularly ozokerite, mineral salts such as sodium chloride or magnesium chloride, silicone polymers such as polysiloxane polyalkyl polyether copolymers.

As examples of spring or mineral waters optionally present in said emulsions of oil-in-water type (C) and (C') as defined previously, there are spring or mineral waters having a mineralization of at least 300 mg/l, in particular Avene water, Vittel water, Vichy basin waters, Uriage water, La Roche Posay water, La Bourboule water, Enghien-les-bains water, Saint-Gervais-les-bains water, Néris-les-bains water, Allevard-les-bains water, Digne water, Maizieres water, Neyrac-les-bains water, Lons le Saunier water, Rochefort water, Saint Christau water, Fumades water and Tercis-les-bains water.

As examples of hydrotropic agents optionally present in said emulsions of oil-in-water type (C) and (C') as defined previously, there are xylene sulfonates, cumene sulfonates, hexyl polyglucoside, (2-ethylhexyl) polyglucoside and n-heptyl polyglucoside.

As examples of deodorants optionally present in said emulsions of oil-in-water type (C) and (C') as defined previously, there are alkali metal silicates, zinc salts such as zinc sulfate, zinc gluconate, zinc chloride or zinc lactate; quaternary ammonium salts such as cetyltrimethylammonium salts or cetylpyridinium salts; glycerol derivatives such as glyceryl caprate, glyceryl caprylate and polyglyceryl caprate; 1,2-decanediol; 1,3-propanediol; salicylic acid; sodium bicarbonate; cyclodextrins; metallic zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

As examples of sunscreens optionally present in said emulsions of oil-in-water type (C) and (C') as defined previously, there are all those listed in the modified cosmetics directive 76/768/EEC, annex VII.

Among the organic sunscreens optionally present in said emulsions of oil-in-water type (C) and (C') as defined previously, there is the family of benzoic acid derivatives, for instance para-aminobenzoic acids (PABA), notably monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA and butyl esters of N,N-dimethyl PABA; the family of anthranilic acid derivatives, for instance homomenthyl-N-acetyl anthranilate; the family of salicylic acid derivatives, for instance amyl salicylate, homomenthyl salicylate, ethylhexyl salicylate, phenyl salicylate, benzyl salicylate and p-isopropanolphenyl salicylate; the family of cinnamic acid derivatives, for instance ethylhexyl cinnamate, ethyl-4-isopropyl cinnamate, methyl 2,5-diisopropyl cinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy-2-ethoxyethyl cinnamate, p-methoxycyclohexyl cinnamate, ethyl-α-cyano-β-phenyl cinnamate, 2-ethylhexyl-α-cyano-β-phenyl cinnamate or glyceryl di-para-methoxymono-2-ethylhexanoyl cinnamate; the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2-carboxylate, 4-hydroxy-2-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5-sulfonic acid and salts thereof; the family of triazine derivatives, for instance hydroxyphenyltriazine, (ethylhexyloxyhydroxyphenyl)(4-methoxyphenyl) triazine, 2,4,6-trianillino(p-carbo-2'-ethylhexyl-1'-oxy)-1,3,5-triazine, 4,4-((6-(((1,1-dimethylethyl)amino)carbonyl)phenyl)amino)-1,3,5-triazine-2,4-diyldiimino)bis-(2-ethylhexyl) benzoate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl) benzotriazole; dibenzazine; dianisoylmethane, 4-methoxy-4"-t-butylbenzoylmethane; 5-(3,3-dimethyl-2-norbornylidene)-3-pentan-2-one; the family of diphenylacrylate derivatives, for instance 2-ethylhexyl 2-cyano-3,3-diphenyl-2-propenoate, ethyl 2-cyano-3,3-diphenyl-2-propenoate; the family of polysiloxanes, for instance benzylidene siloxane malonate.

Among the mineral sunscreens, also known as "mineral sunblocks", optionally present in said emulsions of oil-in-water type (C) and (C') as defined previously, there are titanium oxides, zinc oxides, cerium oxide, zirconium oxide, yellow, red or black iron oxides, and chromium oxides.

These mineral sunblocks may or may not be micronized, may or may not have undergone surface treatments and may optionally be in the form of aqueous or oily predispersions.

As examples of active principles optionally present in said emulsions of oil-in-water type (C) and (C') as defined previously, there are vitamins and derivatives thereof, notably esters thereof, such as retinol (vitamin A) and esters thereof (for example retinyl palmitate), ascorbic acid (vitamin C) and esters thereof, sugar derivatives of ascorbic acid (such as ascorbyl glucoside), tocopherol (vitamin E) and esters thereof (such as tocopheryl acetate), vitamin B3 or B10 (niacinamide and derivatives thereof); compounds showing lightening or depigmenting action on the skin, such as ω-undecelynoyl phenylalanine sold under the name Sepiwhite™ MSH, Sepicalm™ VG, the glyceryl monoester and/or diester of ω-undecelynoyl phenylalanine, ω-undecelynoyl dipeptides, arbutin, kojic acid, hydroquinone; compounds showing a calmative action, such as Sepicalm™ S, allantoin and bisabolol; antiinflammatory agents; compounds showing a moisturizing action, such as urea, hydroxyureas, glycerol glucoside, diglycerol glucoside, polyglyceryl glucosides; polyphenol-rich plant extracts such as grape extracts, pine extracts, wine extracts and olive extracts; compounds showing a slimming or lipolytic action such as caffeine or derivatives thereof, Adiposlim™, Adipoless™, fucoxanthin; N-acyl proteins; N-acyl peptides such as Matrixyl™; N-acylamino acids; N-acyl partial protein hydrolyzates; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; freshwater or marine algal extracts; marine plant extracts; marine extracts in general such as corals; essential waxes; bacterial extracts; ceramides; phospholipids; compounds showing an antimicrobial action or purifying action, such as Lipacide™ C8G, Lipacide™ UG, Sepicontrol™ A5; Octopirox™ or Sensiva™ SC50; compounds showing an energizing or stimulating property such as Physiogenyl™, panthenol and derivatives thereof such as Sepicap™ MP; antiaging active agents such as Sepilift™ DPHP, Lipacide™ PVB, Sepivinol™, Sepivital™, Manoliva™, Phyto-Age™, Timecode™; Survicode™; anti-photoaging active agents; agents for protecting the integrity of the dermo-epidermal junction; agents for increasing the synthesis of components of the extracellular matrix, such as collagen, elastins and glycosaminoglycans; active agents acting favorably on chemical cellular communication, such as cytokines, or physical cellular communication, such as integrins; active agents creating a sensation of "heating" on the skin, such as skin capillary circulation activators (such as nicotinic acid derivatives) or products that create a sensation of "freshness" on the skin (such as menthol and derivatives); active agents which improve the skin capillary circulation, for example venotonic agents; draining active agents; decongestant active agents such as *Ginkgo biloba*, ivy, common horse chestnut, bamboo, Ruscus, butcher's-broom, *Centella asiatica*, fucus, rosemary or willow extracts; skin tanning or browning agents, for instance dihydroxyacetone (DHA), erythrulose, mesotartaric aldehyde, glutaraldehyde, glyceraldehyde, alloxan or ninhydrin, plant extracts, for instance extracts of red woods of the genus *Pterocarpus* and of the genus *Baphia*, for instance *Pterocarpus santalinus, Pterocarpus osun, Pterocarpus soyauxii, Pterocarpus erinaceus, Pterocarpus indicus* or *Baphia nitida*, such as those described in European patent application EP 0 971 683; agents known for their action in facilitating and/or accelerating tanning and/or browning of human skin, and/or for their action in coloring human skin, for instance carotenoids (and more particularly beta-carotene and gamma-carotene), the product sold under the brand name Carrot oil (INCI name: *Daucus carrota, Helianthus annuus* sunflower oil) by the company Provital, which contains carotenoids, vitamin E and vitamin K; tyrosine and/or derivatives thereof, known for their effect on accelerating the tanning of human skin in combination with exposure to ultraviolet radiation, for example the product sold under the brand name SunTan Accelerator™ by the company Provital, which contains tyrosine and riboflavins (vitamin B), the tyrosine and tyrosinase complex sold under the brand name Zymo Tan Complex by the company Zymo Line, the product sold under the brand name Melano-Bronze™ (INCI name: Acetyl Tyrosine, Monk's pepper extract (Vitex Agnus-castus) by the company Mibelle, which contains acetyl tyrosine, the product sold under the trade name Unipertan VEG-24/242/2002 (INCI name: butylene glycol and Acetyl Tyrosine and hydrolyzed vegetable protein and Adenosine triphosphate) by the company Unipex, the product sold under the trade name "Try-Excell™" (INCI name: Oleoyl Tyrosine and Luffa Cylindrica (Seed Oil and Oleic acid) by the company Sederma, which contains extracts of marrow seed (or loofah oil), the product sold under the trade name Actibronze™ (INCI name: hydrolyzed wheat protein and acetyl tyrosine and copper gluconate) by the company Alban Muller, the product sold under the trade name Tyrostan™ (INCI name: potassium caproyl tyrosine) by the company Synerga, the product sold under the trade name Tyrosinol (INCI name: Sorbitan Isostearate, glyceryl oleate, caproyl Tyrosine) by the company Synerga, the product sold under the trade name InstaBronze™ (INCI name: Dihydroxyacetone and acetyl tyrosine and copper gluconate) sold by the company Alban Muller, the product sold under the brand name Tyrosilane (INCI name: Methylsilanol and acetyl tyrosine) by the company Exymol; peptides known for their effect on activating melanogenesis, for example the product sold under the brand name Bronzing SF Peptide Powder (INCI name: Dextran and Octapeptide-5) by the company Infinitec Activos, the product sold under the trade name Melitane (INCI name: Glycerin and Aqua and Dextran and Acetyl hexapeptide-1) comprising the acetyl hexapeptide-1 known for its alpha-MSH agonist action, the product sold under the trade name Melatimes Solutions™ (INCI name: Butylene glycol, Palmitoyl tripeptide-40) by the company Lipotec, sugars and sugar derivatives, for example the product sold under the brand name Tanositol™ (INCI name: Inositol) by the company Provital, the product sold under the brand name Thalitan™ (or Phycosaccharide™ AG) by the company Codif International (INCI name: Aqua and hydrolyzed algin (*Laminaria cigitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna pruriens* Seed extract) by the company Alban Muller, flavonoid-rich compounds, for example the product sold under the brand name Biotanning (INCI name: Hydrolyzed citrus *Aurantium dulcis* fruit extract) by the company Silab and known for being rich in lemon flavonoids (of hesperidin type).

As examples of antioxidants optionally present in said emulsions of oil-in-water type (C) and (C') as defined previously, there is EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S sold by the company AkzoNobel under the INCI name: Tetrasodium Glutamate Diacetate.

DESCRIPTION OF THE PREFERRED EMBODIMENTS

The following examples illustrate the invention without, however, limiting it.

A)—Preparation of Compositions $C_1$ According to the Invention and of Comparative Compositions $C'_1$ A1—Preparation of Compositions $C_1$ According to the Invention The general procedure for the glycosylation reaction performed for preparing the compositions according to the invention is as follows:
- loading the fatty alcohol into a reactor equipped with a mechanical stirrer and a vacuum distillation assembly,
- loading rhamnose monohydrate in powder form in the stoichiometric proportions indicated in tables 1 and 2 below,
- stirring and heating until a "syrup" or "slurry" is obtained,
- placing under partial vacuum to remove the water contained in the rhamnose,
- adding the catalytic system,
- heating until the rhamnose has disappeared,
- if necessary, neutralizing the medium with sodium hydroxide/sodium borohydride mixture, depending on the viscosity of the reaction medium,
- if necessary, filtering the reaction medium.

TABLE 1

| Operating conditions | | |
|---|---|---|
| Initial proportion of stearyl alcohol | 1 molar eq. | 1 molar eq. |
| Initial proportion of rhamnose | 0.2 molar eq. | 1.25 molar eq. |
| Catalyst | $H_2SO_4$ on silica/$H_3PO_2$ | $H_2SO_4$/$H_3PO_2$ |
| Glycosylation temperature | 70° C. | 105° C. |

| Characteristic of the composition obtained (mass %) | | |
|---|---|---|
| | Composition ($C_{1A}$) | Composition ($C_{1B}$) |
| Stearyl polyrhamnoside | 17.0% | 66.5% |
| Mean degree of polymerization (*) | 1.13 | 1.28 |
| Stearyl alcohol | 82.7% | 33.5% |
| Residual rhamnose | 0.3% | 0% |

TABLE 1-continued

| Operating conditions | | |
|---|---|---|
| Initial proportion of stearyl alcohol | 1 molar | 1 molar eq. |
| Initial proportion of rhamnose | 1.25 molar eq. | 2.00 molar eq. |
| Catalyst | $H_2SO_4$ on silica/$H_3PO_2$ | $H_2SO_4$/$H_3PO_2$ |
| Glycosylation temperature | 70° C. | 105° C. |

| Characteristic of the composition obtained (mass %) | | |
|---|---|---|
| | Composition ($C_{1C}$) | Composition ($C_{1D}$) |
| Stearyl polyrhamnoside | 82.5% | 75.0 |
| Mean degree of polymerization (*) | 1.47 | 1.35 |
| Stearyl alcohol | 16.2% | 24.9% |
| Residual rhamnose | 1.3% | 0.1% |

| Operating conditions | | |
|---|---|---|
| Initial proportion of stearyl alcohol | 1 molar eq. | 0 |
| Initial proportion of oleyl alcohol | 0 | 1 molar eq. |
| Initial proportion of rhamnose | 2.0 molar eq. | 1.25 molar eq. |
| Catalyst | $H_2SO_4$ on silica/$H_3PO_2$ | $H_2SO_4$ on silica/$H_3PO_2$ |
| Glycosylation temperature | 70-80° C. | 75° C. |

| Characteristic of the composition obtained (mass %) | | |
|---|---|---|
| | Composition ($C_{1E}$) | Composition ($C_{1F}$) |
| Stearyl polyrhamnoside | 75.5% | 0% |
| Oleyl polyrhamnoside | 0% | 85.0% |
| Mean degree of polymerization (*) | 1.37 | 1.44 |
| Stearyl alcohol | 24% | 0% |
| Oleyl alcohol | 0% | 13.3% |
| Residual rhamnose | 0.5% | 1.7% |

TABLE 2

| Operating conditions | |
|---|---|
| Initial proportion of oleyl alcohol | 1 molar eq. |
| Initial proportion of rhamnose | 2.0 molar eq. |
| Catalyst | $H_2SO_4$ on silica/$H_3PO_2$ |
| Glycosylation temperature | 75-85° C. |

| Characteristic of the composition obtained (mass %) | |
|---|---|
| | Composition ($C_{1G}$) |
| Oleyl polyrhamnoside | 80% |
| Mean degree of polymerization (*) | 1.52 |
| Oleyl alcohol | 0% |
| Residual rhamnose | 18.8% |

(*) the mean degree of polymerization of the polyol rhamnosides is obtained from a gas chromatography, followed by:
i) determining the mass percentages of each oligomer,
ii) normalizing the mass proportions obtained to 100%,
iii) converting into molar percentages the normalized mass percentages obtained, and
iv) calculating the mean degree of polymerization on the basis of each molar percentage obtained, weighted by the number of rhamnose units in the oligomer under consideration.

A2—Preparation of Comparative Compositions C'$_1$

The general procedure for the glycosylation reaction performed for preparing the comparative compositions is as follows:
- loading the fatty alcohol into a reactor equipped with a mechanical stirrer and a vacuum distillation assembly,
- loading glucose monohydrate in powder form in the stoichiometric proportions indicated in table 3 below,
- stirring and heating at 90° C. until a homogeneous "dispersion" is obtained,
- placing under partial vacuum to remove the water contained in the glucose,
- adding the catalytic system,
- heating until the glucose suspension has disappeared,
- if necessary, neutralizing the medium with sodium hydroxide/sodium borohydride mixture, depending on the viscosity of the reaction medium,
- if necessary, filtering the reaction medium.

| Operating conditions | | |
|---|---|---|
| Initial proportion of cetearyl alcohol (**) | 6 molar eq. | 5 molar eq. |
| Initial proportion of glucose | 1 molar eq. | 1 molar eq. |
| Catalyst | H$_2$SO$_4$/H$_3$PO$_2$ | H$_2$SO$_4$/H$_3$PO$_2$ |
| Glycosylation temperature | 105° C. | 105° C. |

| Characteristic of the composition obtained (mass %) | | |
|---|---|---|
| | Composition (C$_{1A}$') | Composition (C$_{1B}$') |
| Cetearyl polyglucosides | 19.0% | 19.8% |
| Mean degree of polymerization (*) | 1.15 | 1.15 |
| Cetearyl alcohol | 81.0% | 80.2% |
| Residual glucose | <0.1% | <0.1% |

| Operating conditions | | |
|---|---|---|
| Initial proportion of cetearyl alcohol | 2 molar eq. | 1 molar eq. |
| Initial proportion of glucose | 1 molar eq. | 1 molar eq. |
| Catalyst | H$_2$SO$_4$/H$_3$PO$_2$ | H$_2$SO$_4$/H$_3$PO$_2$ |
| Glycosylation temperature | 105° C. | 105° C. |

| Characteristic of the composition obtained (mass %) | | |
|---|---|---|
| | Composition (C$_{1C}$') | Composition (C$_{1D}$') |
| Cetearyl polyglucosides | 13.2% | Reaction impossible: the reaction medium sets to a solid |
| Mean degree of polymerization (***) | 1.19 | |
| Cetearyl alcohol | 85.7% | |
| Residual glucose | 1.1% | |

(**) cetearyl alcohol is an equimolar mixture of hexadecyl alcohol (or cetyl alcohol) and of octadecyl alcohol (or stearyl alcohol).
(***) the mean degree of polymerization of the cetearyl polyglucosides is obtained from a gas chromatography, followed by:
i) determining the mass percentages of each oligomer,
ii) normalizing the mass proportions obtained to 100%,
iii) converting into molar percentages the normalized mass percentages obtained, and
iv) calculating the mean degree of polymerization on the basis of each molar percentage obtained, weighted by the number of glucose units in the oligomer under consideration.

It may be noted here that the use of the process of direct glycosylation of fatty alcohols (in this instance cetearyl alcohols) with glucose, similar to that performed for the glycosylation reaction between the fatty alcohols and rhamnose, does not make it possible to obtain compositions according to the invention, irrespective of the molar stoichiometries used.

B)—Determination of the Emulsifying Properties of Compositions According to the Invention Emulsions of oil-in-water type ((E$_1$) to (E$_4$)) are prepared by mixing at 80° C. with stirring 20% by mass of oil and an effective amount of emulsifying composition according to the invention, and the results are compared with that of an oil-in-water emulsion (E$_T$) prepared under the same conditions with Montanov™ 68 (composition (C$_{1T}$) comprising 80% by mass of a mixture of cetyl and stearyl alcohols (50/50 by mass) and 20% by mass of cetearyl polyglucoside). On the basis of its structure, composition (C$_{1T}$) is representative of compositions (C'$_{1A}$) and (C'$_{1B}$) as described above. The data are collated in the following table:

| | O/W emulsion | | | | | | | |
|---|---|---|---|---|---|---|---|---|
| Emulsifier | E$_1$ | E$_2$ | E$_3$ | E$_4$ | E$_{T1}$ | E$_{T2}$ | E$_{T3}$ | E$_{T4}$ |
| Composition (C$_{1C}$) | 2.5% | 2.5% | 3.0% | 3.0% | 0% | 0% | 0% | 0% |
| Composition (C$_{1T}$) | 0% | 0% | 0% | 0% | 2.5% | 2.5% | 3.0% | 3.0% |
| Oil | | | | | | | | |
| Primol™ 352 | 20% | 0% | 20% | 0% | 20% | 0% | 20% | 0% |
| Sweet almond oil | 0% | 20% | 0% | 20% | 0% | 20% | 0% | 20% |
| Water | 77.5% | 77.5% | 77.0% | 77.0% | 77.5% | 77.5% | 77.0% | 77.0% |
| Stability at seven days at room temperature | St*. | St*. | St*. | St*. | Exud.** | Exud.** | St*. | St*. |

*St.: Stable;
**Exud.: Start of exudation

C) Formulations

In the following formulas, the percentages are expressed by weight of the formulation.

C.1 Makeup-Removing Fluid for the Face
Formula

| | | |
|---|---|---|
| Composition ($C_{1B}$) | | 10.00% |
| Methyl paraben | | 0.15% |
| Phenoxyethanol | | 0.80% |
| Sepicalm ™ S | | 1.00% |
| Perfume/Fragrance | | 0.10% |
| Water | | qs 100.00% |

Procedure: Mix the various ingredients in the water with magnetic stirring, in the order indicated, and adjust the pH to about 7.

C.2 Infant Hair and Body Shampoo
Formula

| | | |
|---|---|---|
| A | Composition ($C_{1C}$) | 5.00% |
| | Proteol ™ APL | 5.00% |
| | Sepicide ™ HB | 0.50% |
| | Perfume/Fragrance | 0.10% |
| B | Water | 20.00% |
| | Capigel ™ 98 | 3.50% |
| C | Water | qs 100.00% |
| | Sepicide ™ CI | 0.30% |
| | Colorant | qs |
| | Sodium hydroxide | qs pH = 7.2 |

Procedure: Mix composition ($C_{1C}$) with the Proteol™ APL and the Sepicide™ HB (Phase A). Dilute the Capigel™ 98 in a portion of the water and add it to phase A obtained previously (Phase B). Add the rest of the water to phase B, followed by the Sepicide™ CI and the colorant. Adjust the pH of the mixture to about 7.2 with sodium hydroxide.

C.3 Makeup-Removing Wipes for the Eyes
Formula

| | | |
|---|---|---|
| A | Composition ($C_{1C}$) | 3.00% |
| B | Sepicide ™ HB2 | 0.50% |
| C | Sepicalm ™ VG | 0.50% |
| | Perfume/Fragrance | 0.05% |
| D | Water | qs 100.00% |

Procedure: Mix the ingredients of phase B and those of phase C in phase A until the solution is clear. Add phase D.

C.4 Mild Foaming Gel
Formula

| | | |
|---|---|---|
| A | Composition ($C_{1D}$) | 8.50% |
| | Proteol ™ APL | 3.00% |
| | Euxyl ™ PE9010 | 1.00% |
| | Perfume/Fragrance | 0.10% |
| B | Water | qs 100.00% |
| | Lactic acid | qs pH = 6.0 |

Procedure: Dissolve the perfume and the preserving agent Euxyl™ PE9010 in the mixture composed of composition $E_4$ and the Proteol™ APL (phase A). Add the water and adjust the pH to about 6.0 with lactic acid.

C.5 Regular-Use Shampoo
Formula

| | | |
|---|---|---|
| A | Composition ($C_{1B}$) | 12.80% |
| | Proteol ™ OAT | 5.00% |
| | Euxyl ™ PE9010 | 1.00% |
| | Perfume/Fragrance | 0.30% |
| | Water qs | 100.00% |
| B | Montaline ™ C40 | 8.50% |
| | Lactic acid | qs pH = 6.0 |

Procedure: Mix all the ingredients of phase A and, after homogenization, add the Montaline™ C40 and adjust the pH to about 6.0 with lactic acid.

C.6 Ultra-Mild Baby Shampoo
Formula

| | | |
|---|---|---|
| A | Composition ($C_{1F}$) | 10.00% |
| | Amisoft ™ CS-11 | 4.00% |
| | Perfume/Fragrance | 0.10% |
| | Sepicide ™ HB | 0.30% |
| | Sepicide ™ CI | 0.20% |
| | Water | qs 100.00% |
| B | Water | 20.00% |
| | Capigel ™ 98 | 3.50% |
| | Tromethamine | qs pH = 7.2 |

Procedure: Mix all the ingredients of phase A, in the order indicated, until a clear phase A is obtained. Separately, add the Capigel™ 98 to the water and then add this phase B thus prepared to phase A and adjust the pH to 7.2 using tromethamine.

C.7 Baby Cleansing Milk
Formula

| | | |
|---|---|---|
| A | Simulsol ™ 165 | 2.00% |
| | Montanov ™ 202 | 1.00% |
| | Lanal ™ 99 | 3.00% |
| | Dimethicone | 1.00% |
| | Isohexadecane | 3.00% |
| B | Water | qs 100.00% |
| C | Sepiplus ™ 400 | 0.30% |
| D | Composition ($C_{1B}$) | 6.35% |
| E | Sepicide ™ HB | 0.30% |
| | DMDM Hydantoin | 0.20% |
| | Perfume/Fragrance | 0.10% |

Procedure: Heat, separately, phases A and B constituted by mixing the various constituents. Add phase C to the hot fatty phase and make the emulsion by pouring in the aqueous phase; homogenize for a few minutes with vigorous stirring (by means of a rotor/stator turbomixer). Next, add phase D to the hot emulsion and cool the emulsion with moderate stirring down to room temperature. Add phase E at 40° C.

C.8 Cleansing Powder Lotion for Sensitive Skin
Formula

| | | |
|---|---|---|
| A | Lipacide ™ C8G | 0.95% |
| | Methyl paraben | 0.10% |
| | Ethyl paraben | 0.024% |
| | Propyl paraben | 0.0119% |
| | Butyl paraben | 0.024% |
| | Isobutyl paraben | 0.0119% |
| | Water | 20.00% |
| | Disodium EDTA | 0.10% |
| | Triethanolamine | 1.38% |

| | | |
|---|---|---|
| B | Composition (C$_{1D}$) | 1.80% |
| | Perfume/Fragrance | 0.10% |
| C | Sepicalm ™ S | 0.28% |
| | Water | qs 100.00% |
| | Lactic acid | qs pH = 5.2 |
| D | Micropearl ™ M310 | 5.00% |

Procedure: Dissolve the ingredients of phase A in the water at 80° C. Separately, dissolve the perfume in composition (E$_4$) to prepare phase B. Add the cooled phase A to phase B, then introduce the Sepicalm™ S and the remaining water. Check the final pH and adjust to about 5.2 if necessary. Next, add the Micropearl™ M310.

C.9 Infant Shower Gel
Formula

| | | |
|---|---|---|
| A | Water | 56.06% |
| | Sepimax ™ Zen | 3.00% |
| | Sepiplus ™ S | 0.80% |
| B | Proteol ™ OAT | 20.80% |
| | Oramix ™ NS 10 | 9.30% |
| | Amonyl ™ 265 BA | 5.10% |
| C | Composition (C$_{1C}$) | 2.00% |
| | Glyceryl glucoside | 1.00% |
| | Phenoxyethanol & ethylhexyl glycerol | 1.00% |
| | Perfume/Fragrance | 0.90% |
| | Colorant | 0.04% |

Procedure: disperse the Sepimax™ ZEN in the water and stir using a mechanical stirrer equipped with a deflocculator, a counter-rotating impeller and an anchor paddle, until a perfectly smooth gel is obtained. Add the Sepiplus™ S and then stir until the mixture is homogeneous. Next, add the ingredients of phase B, homogenize and individually add the additives of phase C. Adjust the pH to 6.0-6.5.

C.10 BB Cream
Formula

| | | |
|---|---|---|
| A | Easynov ™ | 2.30% |
| | Lanal ™ 99 | 1.00% |
| | Sepimat ™ H10W | 1.00% |
| | Ethylhexyl methoxycinnamate | 5.00% |
| B | Cyclomethicone | 6.00% |
| | Triethoxycaprylsilane & alumina-silane & titanium oxide | 8.00% |
| | Red iron oxide & triethoxycaprylsilane | 0.24% |
| | Yellow iron oxide & triethoxycaprylsilane | 0.66% |
| | Black iron oxide & triethoxycaprylsilane | 0.09% |
| | Perfume/Fragrance | 0.10% |
| C | Water qs | 100% |
| | Sepinov ™ EMT10 | 1.20% |
| D | Composition (C$_{1D}$) | 2.00% |
| | Sepitonic ™ M3 | 1.00% |
| | Phenoxyethanol & ethylhexyl glycerol | 1.00% |

Procedure: Prepare phase B by mixing the various ingredients and homogenize using a mixer equipped with a rotor-stator system at a spin speed of 4500 rpm, for a time of 6 minutes. Prepare phase C by adding the Sepinov™ EMT10 to the mixture of water and glycerol, and homogenize using a mixer equipped with a rotor-stator system at a spin speed of 4000 rpm for 4 minutes. Add phases A and B to phase C, and stir the resulting mixture using a mechanical stirrer equipped with an anchor paddle, at a speed of 30 rpm for 2 minutes, and then at a speed of 50 rpm for 20 minutes. Add the components of phase 5 one by one and stir at a speed of 50 rpm for 25 minutes.

Sepicalm™ S: Mixture of N-cocoyl amino acids, sarcosine, potassium aspartate and magnesium aspartate as described in WO 98/09611;

Proteol™ APL: Mixture of sodium salts of N-cocoyl amino acids, obtained by acylation of amino acids characteristic of apple juice;

Sepicide™ HB: Mixture of phenoxyethanol, methyl paraben, ethyl paraben, propyl paraben and butyl paraben, which is a preserving agent;

Capigel™ 98: Acrylate copolymer;

Sepicide™ CI: Imidazoline urea, which is a preserving agent;

Sepicide™ HB: Mixture of phenoxyethanol, methyl paraben, ethyl paraben, propyl paraben, butyl paraben and isobutyl paraben, which is a preserving agent;

Sepicalm™ VG: Mixture of N-palmitoyl proline in sodium salt form and of extract of Nymphea alba blossom;

Euxyl™ PE9010: Mixture of phenoxyethanol and ethylhexyl glycerol;

Proteol™ OAT: Mixture of N-lauryl amino acids obtained by total hydrolysis of oat protein as described in WO 94/26694;

Montaline™ C40: Chloride salt of monoethanolamine cocamidopropyl betainamide;

Amisoft™ CS-11: Sodium salt of N-cocoyl glutamate;

Simulsol™ 165: Mixture of PEG-100 stearate and glyceryl stearate;

Montanov™ 202 (arachidyl alcohol, behenyl alcohol and arachidyl glucoside) is a self-emulsifying composition such as those described in EP 0 977 626;

Lanol™99: Isononyl isononanoate;

Sepiplus™ 400: Self-invertible inverse latex of polyacrylates in polyisobutene and including polysorbate 20, as described in WO 2005/040230;

Lipacide™ C8G: Capryloylglycine sold by the company SEPPIC;

Micropearl™ M310: Crosslinked polymethyl methacrylate polymer in powder form, used as a texture modifier;

Sepimax™ Zen (INCI: Polyacrylate Crosspolymer-6): Thickening polymer in the form of a powder;

Sepiplus™ S (INCI name: Hydroxyethyl Acrylate/Sodium Acryloyldimethyl Taurate Copolymer & Polyisobutene & PEG-7 Trimethylolpropane Coconut Ether): Self-invertible inverse latex;

Amonyl™ 265 BA (INCI name: cocoyl betaine): Foaming amphoteric surfactant;

Sepinov™ EMT10 (INCI name: Hydroxyethyl Acrylate/Sodium Acryloyldimethyl Taurate Copolymer): Thickening copolymer in the form of a powder;

Easynov™ (INCI name: Octyldodecanol and Octyldodecyl Xyloside and PEG-30 Dipolyhydroxystearate): Emulsifying agent of lipophilic tendency;

Sepimat™ H10 FW (INCI name: Methyl Methacrylate Crosspolymer and Squalane): Polymer used as texture agent;

Sepitonic™ M3 (INCI name: Magnesium Aspartate and Zinc Gluconate and Copper Gluconate): Mixture used as free-radical scavenger and energizing agent for cells;

Montanov™ L (INCI name: C14-22 Alcohols and C12-20 Alkylglucoside): Emulsifying agent;

Montanov™ 82 (INCI name: Cetearyl Alcohol and Cocoglucoside): Emulsifying agent;

Simulgel™ INS100 (INCI name: Hydroxyethyl Acrylate/Sodium Acryloyldimethyl Taurate Copolymer and isohexadecane and Polysorbate 60): Polymeric thickener.

The invention claimed is:

1. A composition ($C_1$) comprising, per 100% of mass:
   (a)—an amount of greater than 0% by mass and less than or equal to 60% by mass of an alcohol of formula (I): R—OH, in which R represents a linear or branched, saturated or unsaturated hydrocarbon-based radical, which may include at least one hydroxyl function, and including from 14 to 22 carbon atoms or a mixture of alcohols of formula (I);
   (b)—an amount of greater than or equal to 40% and less than 100% by mass of a composition ($C_R$) represented by formula (II): R—O-(Rham)$_x$-H, in which Rham represents a rhamnose residue, R is as defined in formula (I) and x, which indicates the average degree of polymerization of said Rham residue, represents a decimal number greater than 1.0 and less than or equal to 5; or a mixture of compositions ($C_R$), and
   (c)—an amount of greater than 0% by mass and less than or equal to 5% by mass of rhamnose.

2. The composition ($C_1$) as defined in claim 1, wherein, in formulae (I) and (II), R represents a saturated or unsaturated, linear or branched hydrocarbon-based radical including from 16 to 20 carbon atoms.

3. The composition ($C_1$) as defined in claim 2, wherein, in formulae (I) and (II), R represents a saturated or unsaturated, linear or branched hydrocarbon-based radical including from 16 to 18 carbon atoms.

4. The composition ($C_1$) as defined in claim 3, comprising, per 100% of mass:
   (a)—an amount of greater than 0% by mass and less than or equal to 60% by mass of a mixture ($M_1$) comprising, per 100% of mass:
      from 30% by mass to 70% by mass of an alcohol of formula ($I_A$): $R_A$—OH, in which $R_A$ represents a hexadecyl radical, and
      from 70% by mass to 30% by mass of an alcohol of formula ($I_B$): $R_B$—OH, in which $R_B$ represents an octadecyl radical;
   (b)—an amount of greater than or equal to 40% and less than 100% by mass of a mixture ($M_{CR1}$) comprising, per 100% of mass:
      from 30% to 70% by mass of a composition ($C_{RA}$) represented by formula ($II_A$): $R_A$—O-(Rham)$_y$-H, in which Rham represents a rhamnose residue, $R_A$ is as defined in formula ($I_A$) and y represents a decimal number greater than 1.0 and less than or equal to 5; and
      from 70% to 30% by mass of a composition ($C_{RB}$) represented by formula ($II_B$): $R_B$—O-(Rham)$_z$-H, in which Rham represents a rhamnose residue, $R_B$ is as defined in formula ($I_B$) and Z represents a decimal number greater than 1.0 and less than or equal to 5; and
   (c)—an amount of greater than 0% by mass and less than or equal to 5% by mass of rhamnose.

5. The composition ($C_1$) as defined in claim 1, wherein, in formulae (I) and (II), R represents a saturated or unsaturated, linear or branched hydrocarbon-based radical including from 20 to 22 carbon atoms.

6. The composition ($C_1$) as defined in claim 5, comprising, per 100% of mass:
   (a)—an amount of greater than 0% by mass and less than or equal to 60% by mass of a mixture ($M_2$) comprising, per 100% of mass:
      from 30% by mass to 70% by mass of an alcohol of formula ($I_C$): $R_C$—OH, in which $R_C$ represents an eicosyl radical, and
      from 70% by mass to 30% by mass of an alcohol of formula ($I_D$): $R_D$—OH, in which $R_D$ represents a docosyl radical;
   (b)—an amount of greater than 40% by mass and less than 100% by mass of a mixture ($M_{CR2}$) comprising, per 100% of mass:
      from 30% to 70% by mass of a composition ($C_{RC}$) represented by formula ($II_C$): $R_C$—O-(Rham)$_t$-H, in which Rham represents a rhamnose residue, $R_C$ is as defined in formula ($I_C$) and t represents a decimal number greater than 1.0 and less than or equal to 5; and
      from 70% to 30% by mass of a composition ($C_{RD}$) represented by formula ($II_D$): $R_D$—O-(Rham)$_u$-H, in which Rham represents a rhamnose residue, $R_D$ is as defined in formula ($I_D$) and u represents a decimal number greater than 1.0 and less than or equal to 5; and
   (c)—an amount of greater than 0% by mass and less than or equal to 5% by mass of rhamnose.

7. The composition ($C_1$) as defined in claim 1, comprising, per 100% of mass:
   (a)—an amount of greater than 0% by mass and less than or equal to 40% by mass of said alcohol of formula (I) or of said mixture of alcohols of formula (I);
   (b)—an amount of greater than or equal to 60% by mass and less than 100% by mass of said composition ($C_R$) or of said mixture of compositions ($C_R$); and
   (c)—an amount of greater than 0% by mass and less than or equal to 5% by mass of rhamnose.

8. The composition ($C_1$) as defined in claim 7, comprising, per 100% of mass:
   (a)—an amount of greater than 0% by mass and less than or equal to 20% by mass of said alcohol of formula (I) or of said mixture of alcohols of formula (I);
   (b)—an amount of greater than or equal to 80% by mass and less than 100% by mass of said composition ($C_R$) or of said mixture of compositions ($C_R$);
   (c)—an amount of greater than 0% by mass and less than or equal to 3% by mass of rhamnose.

9. The composition ($C_1$) as defined in claim 1, wherein, in formula (II), x represents a decimal number greater than zero and less than or equal to 2.

10. A composition ($C_1$) comprising, per 100% of mass:
   (a)—an amount of greater than 0% by mass and less than or equal to 60% by mass of an alcohol of formula (I): R—OH, in which R represents a linear or branched, saturated or unsaturated hydrocarbon-based radical, which may include at least one hydroxyl function, and including from 14 to 22 carbon atoms or a mixture of alcohols of formula (I); and
   (b)—an amount of greater than or equal to 40% and less than 100% by mass of a composition ($C_R$) represented by formula (II): R—O-(Rham)$_x$-H, in which Rham represents a rhamnose residue, R is as defined in formula (I) and x, which indicates the average degree of polymerization of said Rham residue, represents a decimal number greater than 1.0 and less than or equal to 5; or a mixture of compositions ($C_R$).

11. The composition ($C_1$) as defined in claim 7, comprising, per 100% of mass:
   (a)—an amount of greater than 0% by mass and less than or equal to 20% by mass of said alcohol of formula (I) or of said mixture of alcohols of formula (I); and
   (b)—an amount of greater than or equal to 80% by mass and less than 100% by mass of said composition ($C_R$) or of said mixture of compositions ($C_R$).

12. The composition ($C_1$) as defined in claim 2, wherein, in formula (II), x represents a decimal number greater than zero and less than or equal to 2.

13. A topical cosmetic or dermocosmetic emulsion of oil-in-water type (C), comprising, as emulsifier, an effective amount of composition ($C_1$) as defined in claim 1.

14. A topical pharmaceutical or dermopharmaceutical emulsion of oil-in-water type (C'), comprising, as emulsifier, an effective amount of composition ($C_1$) as defined in claim 1.

15. A process for preparing composition ($C_1$) as defined in claim 1, comprising:
   a step a) of heating, with gentle stirring, alcohol of formula (I), or a mixture of said alcohols of formula (I), until reaching a higher temperature ($T_1$) of at least 5° C. above a melting point of the alcohol or the mixture of alcohols to form a molten medium;
   a step b) of dispersing, with stirring, rhamnose monohydrate in the previously molten medium in a desired stoichiometric ratio to form a medium;
   a step c) of acetalization by adding, with stirring, to the medium obtained from step b), a catalytic amount of strong acid, while maintaining under partial vacuum and distilling off any water formed to form a reaction mixture;
   a step d) of filtering the reaction mixture obtained in step c) to form a solution, and,
   a step e) of neutralizing the solution obtained on conclusion of step d), to obtain said composition ($C_1$).

16. A method for preparing emulsions of oil-in-water type, comprising providing the composition ($C_1$) as in claim 1, and forming an emulsion comprising the composition.

17. A process for preparing composition ($C_1$) as defined in claim 1, comprising:
   a step a) of heating, with gentle stirring, alcohol of formula (I), or a mixture of said alcohols of formula (I), until reaching a higher temperature ($T_1$) of at least 5° C. above a melting point of the alcohol or the mixture of alcohols to form a molten medium;
   a step b) of dispersing, with stirring, rhamnose monohydrate in the previously molten medium in a desired stoichiometric ratio to form a medium;
   a step c) of acetalization by adding, with stirring, to the medium obtained from step b), a catalytic amount of strong acid, while maintaining under partial vacuum and distilling off any water formed to form a reaction mixture; and
   a step d) of filtering the reaction mixture obtained in step c).

* * * * *